United States Patent
Duggal et al.

(10) Patent No.: US 11,931,382 B2
(45) Date of Patent: Mar. 19, 2024

(54) GENERATING CIK NKT CELLS FROM CORD BLOOD

(71) Applicant: ImmunityBio, Inc., San Diego, CA (US)

(72) Inventors: Rohit Duggal, San Diego, CA (US); Ranjeet Sinha, San Diego, CA (US)

(73) Assignee: ImmunityBio, Inc., San Diego, CA (US)

( * ) Notice: Subject to any disclaimer, the term of this patent is extended or adjusted under 35 U.S.C. 154(b) by 0 days.

(21) Appl. No.: 17/856,997

(22) Filed: Jul. 3, 2022

(65) Prior Publication Data

US 2022/0347218 A1  Nov. 3, 2022

Related U.S. Application Data

(63) Continuation of application No. 17/260,544, filed as application No. PCT/US2019/040145 on Jul. 1, 2019.

(60) Provisional application No. 62/696,131, filed on Jul. 10, 2018.

(51) Int. Cl.
*A61K 35/17* (2015.01)
*A61K 9/00* (2006.01)
*A61K 39/395* (2006.01)
*C12N 5/0783* (2010.01)

(52) U.S. Cl.
CPC ........... *A61K 35/17* (2013.01); *A61K 9/0019* (2013.01); *A61K 39/395* (2013.01); *C12N 5/0646* (2013.01); *C12N 2501/2302* (2013.01); *C12N 2501/2307* (2013.01); *C12N 2501/2315* (2013.01); *C12N 2501/26* (2013.01); *C12N 2501/51* (2013.01); *C12N 2501/515* (2013.01); *C12N 2501/998* (2013.01)

(58) Field of Classification Search
None
See application file for complete search history.

(56) References Cited

U.S. PATENT DOCUMENTS

| | | |
|---|---|---|
| 2008/0254037 A1* | 10/2008 | Linden ............... C07K 16/2803 424/152.1 |
| 2013/0059379 A1* | 3/2013 | Schmidt-Wolf ..... C12N 5/0646 435/372.3 |
| 2017/0029777 A1* | 2/2017 | Pillai ...................... A61K 35/17 |
| 2017/0042939 A1 | 2/2017 | Zhang |
| 2020/0199532 A1* | 6/2020 | Wald .................... C12N 5/0646 |

FOREIGN PATENT DOCUMENTS

| | | |
|---|---|---|
| CN | 104017770 B | 4/2015 |
| WO | 2011052638 A1 | 5/2011 |

OTHER PUBLICATIONS

International Search Report and Written Opinion from PCT/US2019/040145, dated Nov. 22, 2019, 19 pages.
Gütgemann, et al., "Cytokine-indicued killer cells are type II natural killer T cells," GMS German Medical Science 2007, vol. 5, pp. 1-4.
Li, et al., "Optimized Protocols for Generation of Cord Blood-derived Cytokine-induced Killer/Natural Killer Cells," Anticancer Research 2010, 30: 3493-3500.
Vu, et al., "Culture and differentiation of cytokine-induced killer cells from umbilical cord blood-derived mononuclear cells," Biomedical Research and Therapy 2016, 3(1): 460-468.
Lin, et al., "Interleukin-15 enhances the expansion and function of natural killer T cells from adult peripheral and umbilical cord blood," 2015, 76 348-355.

* cited by examiner

*Primary Examiner* — Michail A Belyavskyi
(74) *Attorney, Agent, or Firm* — Kilpatrick Townsend & Stockton LLP (57) ABSTRACT

Provided herein are methods and customized media compositions for culturing CIK NKT cells.

15 Claims, 4 Drawing Sheets

GENERATING CIK NKT CELLS FROM CORD BLOOD

CROSS-REFERENCE TO RELATED APPLICATIONS

This application is a continuation of U.S. application Ser. No. 17/260,544, filed Jan. 14, 2021, which is a 371 National Phase of PCT/US2019/040145, filed Jul. 1, 2019, which claims priority benefit of U.S. Provisional Application No. 62/696,131 filed Jul. 10, 2018, each of the aforementioned applications is herein incorporated by reference in its entirety for all purposes.

BACKGROUND

Natural killer T cells (NKT cells) represent a subset of T lymphocytes that express natural killer (NK) cell surface markers. A subset of NKT cells, termed invariant NKT cells (iNKT), express a highly restricted T cell receptor (TCR). Although iNKT cells play an important role in linking innate and adaptive immune responses and have been implicated in various diseases, such as infectious diseases, allergy, asthma, autoimmunity, and tumor surveillance (Juno et al. PLoS Pathog. 2012; 8(8)), their activation typically requires CD1d-restricted lipid ligands alpha-galactosylceramide (Gal-Cer). Procedures necessary to introduce Gal-Cer (e.g., in the form of a Gal-Cer/CD1d tetramer) could significantly increase the cost of the treating patients using these NKT cells and in some cases limit the scope of their therapeutical utility. Thus, a need remains for a safe and cost-effective NKT cell therapy that can be used to treat patients having a broad range of tissue types.

BRIEF SUMMARY

Provided herein are CIK NKT cells that can be activated in the absence of Gal-Cer. In some embodiments, greater than 50% of the cells in the CIK NKT cell population express CD56 and CD3 and less than 10% of the cells in the population express Va24. Also provided are compositions and kits comprising a plurality of CIK NKT cells from the population. Methods of producing the CIK NKT cells and using the cells to treat cancer are also provided.

This disclosure provides a population of CIK NKT cells, wherein greater than 50% of the cells in the population express CD 56 and CD3 and less than 10% of the cells in the population express Va24.

Optionally, the population of CIK NKT cells can kill a target cell in the absence of alpha-galactosylceramide (Gal-Cer). Optionally, the target cell is a cancer cell. The cancer cell line may be selected from the group consisting of a myelogenous leukemia cell, a medulloblastoma cell, and a monocytic cell. Optionally, the cancer cell is selected from the group consisting of a K562 cell, a Daudi cell, a DAOY cell, and a THP-1 cell.

Optionally, the CIK NKT cells kill a plurality of the target cells at an EC50 of between 1.0 and 10.0. Optionally, the CIK NKT cells can kill the target cells at a EC50 that is no less than 90% and no greater than 110% of the IC50 at which the CIK NKT cells killing the target cells in the presence of Gal-Cer.

This disclosure also provides a composition comprising a plurality of CIK NKT cells from any of the populations of CIK NKT cells described above, and a physiologically acceptable excipient.

Also provided is a kit for treating cancer comprising a plurality of CIK NKT cells from any of the populations of CIK NKT cells described above and a container and/or a label indicating the kit is for treating cancer.

Also provided is a method of enriching CIK NKT cells from a cord blood sample, the method comprising: isolating mononuclear cells from the cord blood sample; and contacting the isolated mononuclear cells with one or more agents selected from the group consisting of IL-7, ALT-803 or IL-15, FLT3 ligand, and Gal-Cer, whereby enriching CIK NKT cells. IL-7, if present, may be in a concentration ranging from 5 to 20 ng/mL. ALT-803, if present, may be in a concentration ranging from 100 to 300 ng/mL. FLT3 ligand, if present, may be in a concentration ranging from 5 to 20 ng/mL. Gal-Cer, if present, may be in a concentration ranging from 2 to 10 µg/mL.

Optionally, the method further comprises isolating the enriched CIK NKT cells from the rest of the cord blood sample. Optionally, the method further comprises contacting the isolated CIK NKT cells with anti-CD3, anti-CD28, and IL2 to expand the CIK NKT cells. Optionally, the method further comprises contacting the separated CIK NKT cells with Gal-Cer. Optionally, the Gal-Cer is used in a form of a Gal-Cer loaded CD1d tetramer. Optionally, the anti-CD3 antibody may be present in an amount of 5 ng/mL to 60 ng/mL. Optionally, the anti-CD28 antibody is present in an amount of 0.1 µg/mL to 2 µg/mL. Optionally, IL-2 is present in a concentration of 50 ng/mL to 500 ng/mL. Optionally, enriching and/or expansion of CIK NKT cells does not include interferon-gamma.

Also provided is a population of CIK NKT cells produced by the methods of enriching, isolating and expanding CIK NKT cells described above.

Also provided is a method of treating cancer or viral infection in a patient in need thereof, the method comprising administering to the patient a therapeutically effective amount of CIK NKT cells from any of the populations of CIK NKT cells as described above, thereby treating cancer. Optionally, $1 \times 10^8$ to about $1 \times 10^{11}$ CIK NKT cells per m$^2$ of body surface area of the patient are administered to the patient. Optionally, the cancer is selected from the group consisting of a leukemia, a lymphoma, polycythemia vera, multiple myeloma, Waldenstrom's macroglobulinemia, heavy chain disease, a sarcoma and a carcinoma. Optionally the cells are administered to the patient by a route selected from the group consisting of intravenous, intraperitoneal, and subcutaneous. Optionally, the method further comprises administering an antibody.

Also provided is a population of CIK NKT cells of claim 1, wherein the CIK NKT cells express a CAR and/or a cytokine, and greater than 50% of the cells in the CIK NKT cell population express CD56 and CD3 and less than 10% of the cells in the population express Va24.

The foregoing general description and the following detailed description are exemplary and explanatory and are intended to provide further explanation of the disclosure. Other objects, advantages and novel features will be readily apparent to those skilled in the art.

BRIEF DESCRIPTION OF THE DRAWINGS

The objects, features and advantages will be more readily appreciated upon reference to the following disclosure when considered in conjunction with the accompanying drawings.

FIG. 2A shows the results of flow cytometry analysis of CIK NKT cells stained with CD3, CD56, and Va24.

DETAILED DESCRIPTION

Overview

This application provides cytokine induced killer NKT cells (CIK NKT cells) that can kill target cells in a non-CD1d restricted manner, i.e., independent of the formation of the Gal-Cer/CD1d tetramer. The CIK NKT cells can be used to target a broad range of target cells and will not trigger Graft-versus-host disease (GVHD). GVHD occurs due to invasive ability of lymphocytes to infiltrate and cause extensive inflammation in organs such as the gut, skin and liver. It has been shown that CIK NKTs do not express chemokine receptors important for targeting to GVHD organs but do express receptors that facilitate homing to tumors, thus they will not trigger GVHD. As compared to existing technologies of generating CIK NKT cells, which normally produce a heterogenous population consisting of CD3+, CD56+ single positive cells and CD3+/CD56+ double positive cells, and the double positive cells typically 30% or less, the present methods produce a cell population that consists of predominantly CD3+/CD56+ double positive cells. In one aspect, at least 50% of the CIK NKT cells in the population express both CD56 and CD3 and less than 10% of the cells in the population express Va24. The method of producing CIK NKT cells do not require the exposing the cells to interferon-gamma, which saves cost. Thus, the application provides a safe and cost-effective NKT cell therapy that can be used broadly to treat various diseases, e.g., cancers, without causing clinically adverse symptoms such as GVHD.

The disclosure also provides compositions and kits comprising a plurality of CIK NKT cells from the population. Methods of producing the CIK NKT cells and using the CIK NKT cells to treat cancer are also provided.

Terminology

Unless defined otherwise, all technical and scientific terms used herein have the same meaning as commonly understood by one of ordinary skill in the art.

In this specification and in the claims that follow, reference will be made to a number of terms that shall be defined to have the following meanings:

The terminology used herein is for the purpose of describing particular embodiments only and is not intended to be limiting. As used herein, the singular forms "a," "an" and "the" are intended to include the plural forms as well, unless the context clearly indicates otherwise. Thus, for example, reference to "a natural killer cell" includes a plurality of natural killer cells.

All numerical designations, e.g., pH, temperature, time, concentration, amounts, and molecular weight, including ranges, are approximations which are varied (+) or (−) by increments of 0.1 or 1.0, where appropriate. It is to be understood, although not always explicitly stated, that all numerical designations may be preceded by the term "about."

As used herein, "+", when used to indicate the presence of a particular cellular marker, means that the cellular marker is detectably present in fluorescence activated cell sorting over an isotype control; or is detectable above background in quantitative or semi-quantitative RT-PCR.

As used herein, "−", when used to indicate the presence of a particular cellular marker, means that the cellular marker is not detectably present in fluorescence activated cell sorting over an isotype control; or is not detectable above background in quantitative or semi-quantitative RT-PCR.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claims. "Consisting of" shall mean excluding more than trace amount of other ingredients and substantial method steps. Embodiments defined by each of these transition terms are within the scope of the disclosure.

As used herein, the terms "cytotoxic" and "cytolytic", when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

The term "kill" with respect to a cell/cell population is directed to include any type of manipulation that will lead to the death of that cell/cell population.

The term "cytokine" or "cytokines" refers to the general class of biological molecules which effect cells of the immune system. Exemplary cytokines include but are not limited to FLT3 ligand, interferons and interleukins (IL), in particular IL-2, IL-12, IL-15, IL-18 and IL-21.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. The term "administering" or "administration" of a monoclonal antibody or a natural killer cell to a subject includes any route of introducing or delivering the antibody or cells to perform the intended function. Administration can be carried out by any route suitable for the delivery of the cells or monoclonal antibody. Thus, delivery routes can include intravenous, intramuscular, intraperitoneal, or subcutaneous delivery. In some embodiments the CIK NKT cells are administered directly to the tumor, e.g., by injection into the tumor. In some embodiments the modified CIK NKT cells described herein are administered parenterally, e.g., by injection, infusion or implantation (subcutaneous, intravenous, intramuscular, intravesicularlly, or intraperitoneal).

The term "expression" refers to the production of a gene product.

As used herein, the terms "cytotoxic" when used to describe the activity of effector cells such as NK cells, relates to killing of target cells by any of a variety of biological, biochemical, or biophysical mechanisms.

The terms "decrease," "reduced," "reduction," and "decrease" are all used herein to refer to a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The term "therapeutically effective amount" or "effective amount" refers to the amount required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

Titles or subtitles may be used in the specification for the convenience of a reader, which are not intended to influence the scope of the present disclosure. Additionally, some terms used in this specification are more specifically defined below.

Cytokine Induced Killer Natural Killer T Cells (CIK NKT Cells)

Natural killer T cells are a heterogeneous group of T cells that share properties of both T cells and natural killer cells. For example, NKT cells express an alpha beta T-cell receptor, but also express a variety of molecular markers that are typically associated with NK cells, such as NKp44, NKp46, and NKp30. NKT cells constitute only about 0.1% of all peripheral blood T cells. NKT cells have been implicated in suppression of autoimmunity and graft rejection, promotion of resistance to pathogens, and promotion of tumor immunity.

NKT cells are typically classified into type I and type II, based on differences in T cell receptor (TCR) usage. Type 1 NKT cells, also commonly referred to as invariant NKT cells, are NKT cells that express a highly restricted T cell receptor, which comprises an invariant TCR alpha chain, Va24.

Invariant NKT cells are typically activated by recognizing lipid ligands alpha-galactosylceramide (Gal-Cer) presented by CD1d. CD1d is a member of CD1 family of glycoproteins expressed on the surface of various antigen presenting cells and are involved in the presentation of lipid antigens. In contrast to class I and II major histocompatibility complex (MHC) molecules that present protein antigens to CD8+ and CD4+ T cells, respectively, CD1 molecules can capture and process both foreign and self lipid antigens for display to T cells. Gal-Cer are typically derived from pathogenic cells, for example, bacteria.

As compared to Type I NKT cells, type II NKT cells have a more diverse TCR repertoire and a higher sequence diversity. Type II NKT cells do not respond to Gal-Cer, i.e., their activation is independent of the presence of Gal-Cer.

Figure 3A:
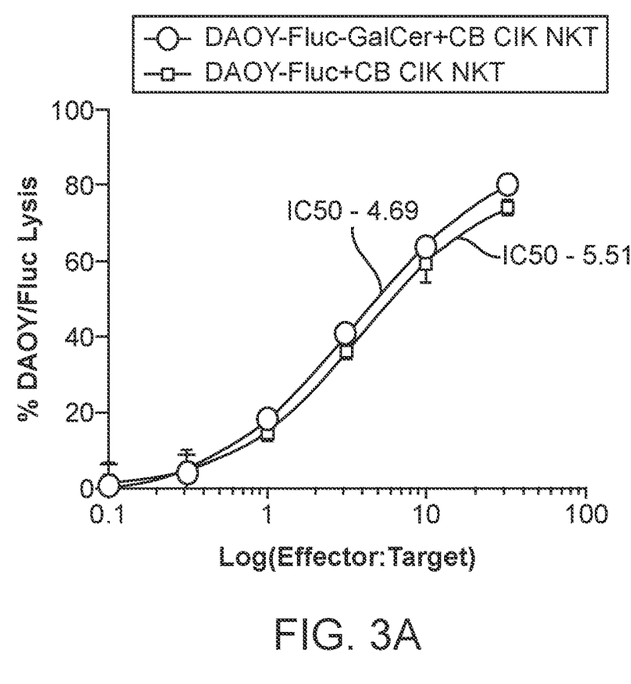
FIG. 3A shows the killing of DAOY cells in the presence (represented by circles) or absence (represented by squares) by the cord blood CIK NKT cells.
Figure 3B:
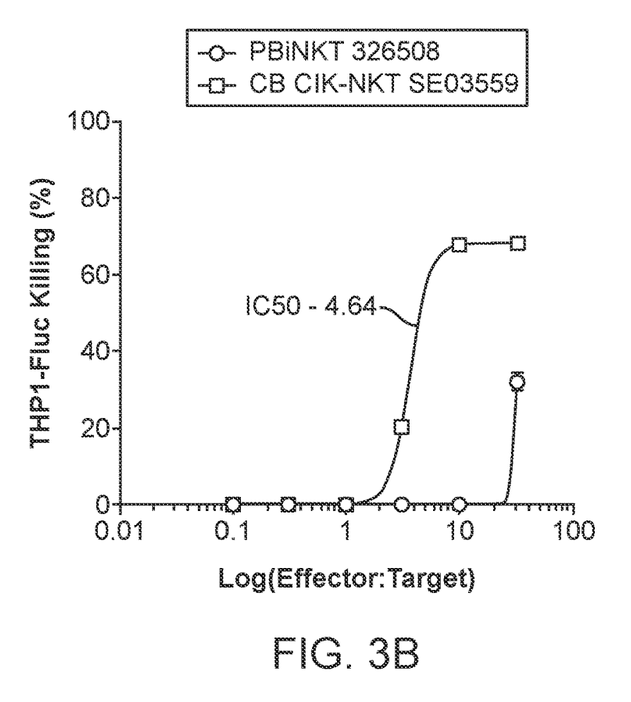
FIG. 3B shows the killing of luciferase-expressing THP1 cells by cord blood CIK NKT cells (represented by squares) or peripheral blood iNKT cells (represented by circles).

The CIK NKT cells disclosed herein belong to the category of type II NKT cells. The CIK NKT cells can be produced through cytokine induction. In some instances, they are produced from e.g., cord blood, through cytokine induction. In some instances they are produced during the process of enriching or isolating iNKT cells from cord blood samples. However, CIK NKT cells differ from the typical iNKT cells in several aspects. Phenotypically, unlike iNKT cells, which express Va24, a marker for the alpha chain of a TCR receptor, and the percentage of iNKT cells that express Va24 is can be 70% or higher, CIK NKT cells have reduced expression of Va24. For example, the percentage of CIK NKT cells that express Va24 may be less than 10% of the total population of CIK NKT cells. In terms of cytotoxicity, unlike iNKT cells, which are activated by recognizing the alpha galactosyl ceramide (Gal-Cer), a glycolipid, the CIK NKT cells do not need Gal-Cer to be activated and can kill the cells in the absence of (Gal-Cer). See FIG. 3 and FIG. 4.

Thus, in terms of phenotypes, the CIK NKT cells provided herein typically have high expression levels of CD56 and CD3 and low expression of Va24. In some instances, at least 90% of the CIK NKT population produced from the cord blood cells express CD56 and CD3, and less than 10% of the cells in the population express Va24.

Method of Isolating and Culturing CIK NKT Cells

Collecting Cord Blood

Human umbilical cord blood has high composition of hematopoietic stem cells and can be used as a source for generating CIK NKT cells. To collect cord blood, generally, a human placenta is recovered shortly after its expulsion after birth. The placenta can be transported in a sterile, thermally insulated transport device (maintaining the temperature of the placenta between 20-28° C.), for example, in a cord blood collection kit substantially as described in U.S. Pat. No. 7,147,626. Preferably, the placenta is delivered to the laboratory four to twenty-four hours following delivery.

The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and CryoCell. Preferably, the placenta is gravity drained without further manipulation so as to minimize tissue disruption during cord blood recovery.

Methods for collecting cord blood cells are well known, for example, as described in US20150225697. Cord blood mononuclear cells (Comics) can be isolated from collected cord blood using methods well known in the art, e.g., a density gradient method using Ficoll-Pague. Reagents suitable for isolating Comics are commercially available, e.g., from Stem cell Technology Inc.

Enriching CIK NKT Cells

Comics can be cultured for a period of time in the presence of various cytokines in order to enrich for CIK NKT cells. Enriching refers to increasing the percentage of number of target cells in a heterogenous cell population (e.g., the Comics). The enrichment period may be 2 days-3 weeks, e.g., 1-2 weeks, 5-10 days, or about 2 weeks. Various growth media can be used, for example, Roswell Park Memorial Institute medium (RPMI), or Dulbecco's modified eagle medium (DMEM). Optionally, the medium further comprises human AB serum and/or Gal-Cer. Optionally, the human AB serum is present in 5-15% v/v, e.g., about 10% v/v. Optionally, the Gal-Cer is present in a concentration of 2-10 µg/mL, e.g., about 5 µg/mL. Suitable cytokines that can be added to the medium may include one or more cytokines selected from the group consisting of stem cell factor, FLT3 ligand, IL-7, and ALT-803 or IL-15. In some embodiments, FLT3 ligand is present in a concentration ranging from 5-20 ng/mL, e.g., 10 ng/mL; IL-7 is present in a concentration ranging from 5-20 ng/mL, e.g., 10 ng/mL; and/or ALT-803 is present in a concentration ranging from 100-300 ng/mL, e.g., about 175 ng/mL.

FLT3 ligand is a hematopoietic four helical bundle cytokine and it is structurally homologous to stem cell factor (SCF) and colony stimulating factor 1 (CSF-1). In synergy with other growth factors, FLT3 ligand stimulates the proliferation and differentiation of various blood cell progenitors. It is a major growth factor stimulating the growth of dendritic cells.

ALT-803 is a complex consisting of human IL-15 mutant IL-15N72D (residue substitution at position 72) and IL-15Rα sushi-Fc fusion protein (see Zhu et al. J. Immunol. 2009; 183:3598-607, the relevant disclosure is hereby incorporated by reference).

CIK NKT cells can be isolated from the enriched culture described above by methods well known in the art, for example, incubating magnetic beads coupled with antibody against the Va24-J18 chain of the TCR with the enriched culture so that the CIK NKT cells will bind to the magnetic beads, and subsequently isolating the CIK NKT cells that are bound to the beads in presence of a magnetic field. One example of the suitable antibodies that can be used is the 6B11 antibody, which are commercially available for vendors such as Biolegend (San Diego, CA). Suitable reagents for isolating CIK NKT cells are from Miltenyi Biotec, Germany. CIK NKT cells are typically isolated in PBS-containing serum (e.g., human AB serum). Optionally, the isolation solution also contains EDTA.

Thus, provided herein is a method of enriching CIK NKT cells from cord blood, the method comprising: from a cord blood sample, the method comprising: isolating mononuclear cells from the cord blood sample; and contacting the isolated monocytes with one or more agents selected from the group consisting of IL-7, ALT-803, FLT3 ligand, and Gal-Cer to enrich CIK NKT cells.

Expanding CIK NKT Cells

The CIK NKT cells as isolated above can be expanded in suitable growth medium. Expanding refers to growing an isolated population of target cells so that the target cells increase in number. In some embodiments, the growth medium is the NK Macs medium, available from Miltenyi Biotec, Germany. In some embodiments, the growth medium is supplemented with IL-2, anti-CD3, and/or anti CD28 antibodies in amounts suitable for NKT cell growth. In some embodiments, the anti-CD3 antibody is present in a concentration of 5 ng/mL to 60 ng/mL, e.g., 20 ng/mL. In some embodiments, the anti-CD28 antibody is present in a concentration of 0.1 µg/mL to 2 µg/mL, e.g., 0.5 µg/mL. In some embodiments, IL-2 is present in a concentration of 50 ng/mL to 500 ng/mL, e.g., 200 ng/mL. In some embodiments, the growth medium comprises human AB serum (e.g., about 10% v/v). In some embodiments, the growth medium further comprises a Gal-Cer loaded CD1d tetramer. In some embodiments, the Gal-Cer loaded CD1d tetramer is a pre-assembled tetramer that are commercially available, e.g., from ProImmune (Oxford, UK). Methods for assembling Gal-Cer loaded CD1d tetramer is well known. Typically, Gal-Cer lipid is co-incubated with CD1d protein, which are oligomerized on streptavidin surface to become tetramers. Upon Gal-Cer binding to CD1d complex, it was column purified and used as reagents for expansion. Some of the exemplary methods for preparing the Gal-Cer loaded CD1d tetramers are described in www.proimmune.com/ecommerce/pdf_files/PS_DE000-RPE_V1.1%20%28CD-1d%20Tetramer%20Empty%20%28R-PE%20Labeled%29%29.pdf and proimmune.com/ecommerce/pdf_files/ST14.pdf. In some embodiments, the Gal-Cer loaded CD1d tetramer is used at an amount such that the concentration of the Gal-Cer in the growth medium is about 20-200 ng/mL, e.g., 50-150 ng/mL, or 80-120 ng/mL, or about 100 ng/mL of Gal-Cer. In some embodiments, the CIK NKT cells are let grown and expanded for over a few days or weeks to reach a suitable amount of cells for various applications.

Accordingly, the disclosure provides a method of growing CIK NKT cells from cord blood, the method comprising:

from a cord blood sample, the method comprising: isolating mononuclear cells from the cord blood sample; and contacting the isolated monocytes with one or more agents selected from the group consisting of IL-7, ALT-803, FLT3 ligand, and Gal-Cer to enrich CIK NKT cells.

Phenotyping the CIK NKT Cells

In certain embodiments, a CIK NKT cell populations can be assessed by detecting one or more functionally relevant markers, for example, CD56 and CD3 (markers for NKT cells) and TCR receptor Va24 (a high expression of which indicates the NKT cells are invariant NKT cells).

In some embodiments, provided herein are a CIK NKT cell population comprising a lower percentage of Va24+ cells as compared to typical invariant NKT cells. The CIK NKT cell population comprises about 4%, about 5%, about 6%, about 7%, about 8%, about 9%, or about 10% of Va24+ cells. In some embodiments, the CIK NKT cell population comprises between 0-20%, 5-10%, 1-7%, or 4-8% Va24+ cells. In some embodiments, the CIK NKT cell population comprises no more than 20%, no more than 15%, no more than 10% of the Va24+ cells.

In some embodiments, provided herein are a CIK NKT cell population comprising a percentage of CD56+ cells that is substantially similar to that in a typical invariant NKT cell population. The CIK NKT cell population comprises at least about 50%, at least about 60%, at least about 70%, at least about 80%, at least about 90%, at least about 95%, at least about 96%, at least about 97%, at least about 98%, or about 99% of CD56+cells. In some embodiments, the CIK NKT cell population comprises between 50-100%, 70-100%, 85-100%, 90-100%, 95-100%, or 98-100% CD56+ cells. In some embodiments, the CIK NKT cell population comprises no less than 50%, no less than 70%, no less than 85%, no less than 90%, no less than 93%, or no less than 95% of the CD56+ cells.

In some embodiments, provided herein are a CIK NKT cell population comprising a percentage of CD3+ cells that is substantially similar to that in a typical invariant NKT cell population. The CIK NKT cell population comprises at least about 50%, at least about 60%, at least about 70%, at least about 80%, at least about 90%, at least about 95%, at least about 96%, at least about 97%, at least about 98%, or about 99% of CD3+cells. In some embodiments, the CIK NKT cell population comprises between 50-100%, 70-100%, 85-100%, 90-100%, 95-100%, or 98-100% of the CD3+ cells. In some embodiments, the CIK NKT cell population comprises no less than 50%, no less than 70%, no less than 85%, no less than 90%, no less than 93%, or no less than 95% of the CD3+ cells.

In some embodiments, provided herein are a CIK NKT cell population comprising a percentage of CD56+ CD3+ cells that is substantially similar to that in a typical invariant NKT cell population. The CIK NKT cell population comprises at least about 50%, at least about 60%, at least about 70%, at least about 80%, at least about 90%, at least about 95%, at least about 96%, at least about 97%, at least about 98%, or about 99% of CD56+CD3+ cells. In some embodiments, the CIK NKT cell population comprises between 50-100%, 70-100%, 85-100%, 90-100%, 95-100%, or 98-100% of the CD56+CD3+cells. In some embodiments, the CIK NKT cell population comprises no less than 50%, no less than 70%, no less than 85%, no less than 90%, no less than 93%, or no less than 95% of the CD56+CD3+cells.

Cytotocicity of the CIK NKT Cells

Optionally, the cytotoxic activity isolated or enriched natural killer cells can be assessed, e.g., in a cytotoxicity assay using tumor cells, e.g., cultured K562, DAOY, THP-1, LN-18, U937, WERI-RB-1, U-118MG, HT-29, HCC2218, KG-1, or U266 tumor cells, or the like as target cells. CIK NKT cells disclosed herein can kill target cells regardless of MHC type and regardless of the presence of αGal-Cer.

Assays for evaluating cytotoxicity are well known, for example, MTT assay. This is a system based on the tetrazolium compound MTT. Briefly, after the treatment period in which the target cells are in contact with CIK NKT cells, 10 uL of a freshly diluted MTT solution (2.5 mg mL$^{-1}$) was added to each well, and the plate was incubated at 37 C in a humidified 5% CO2 atmosphere for 4 h. At the end of the incubation period, the medium was removed, and the formazan product was dissolved in 100 µL of dimethyl sulfoxide. Cell viability was evaluated by measurement of the absorbance at 570 nm, using a SUNRICE Tecan absorbance reader (Schoeller). Compound concentrations that produce 50% cell growth inhibition (IC50) were calculated from curves constructed by plotting cell survival (%) versus drug concentration (µM). The reading values were converted to the percentage of the control (percentage cell survival). Non-limiting methods of cell killing assays include Sulphorhodamine B (SRB) assay, Neutral red (NR) assay, such as those described in www.rsc.org/suppdata/mt/c4/c4mt00112e/c4mt00112e1.pdf, herein incorporated by reference in its entirety.

The efficacy of the CIK NKT cells on killing target cells can be evaluated with an EC50. EC50 used in this disclosure refers to the effector to target ratio used in an assay where 50% of target cells are killed. In some embodiments, the CIK NKT cells is able to kill a plurality of the target cells at an EC50 of 1-10, e.g., 1-8, 2-6, 2-5.5, or 3-7. In some embodiments, the target cell is THP-1 and the EC50 is 4.64. In some embodiments, the target cell is DAOY and the IC50 is 3.69. In some embodiments, the target cell is K562 and the IC50 is 2.6.

Modified CIK NKT Cells

Chimeric Antigen Receptor

The CIK NKT cells produced as above can be further engineered to express a chimeric antigen receptor (CAR) on the cell surface. Optionally, the CAR is specific for a tumor-specific antigen. Tumor-specific antigens are described, by way of non-limiting example, in US 2013/0189268; WO 1999024566 A1; U.S. Pat. No. 7,098,008; and WO 2000020460 A1, each of which is incorporated herein by reference in its entirety. Tumor-specific antigens include, without limitation, NKG2D, CS1, GD2, CD138, EpCAM, EBNA3C, GPA7, CD244, CA-125, ETA, MAGE, CAGE, BAGE, HAGE, LAGE, PAGE, NY-SEO-1, GAGE, CEA, CD52, CD30, MUCSAC, c-Met, EGFR, FAB, WT-1, PSMA, NY-ESO1, AFP, CEA, CTAG1B, CD19 and CD33. Additional non-limiting tumor-associated antigens, and the malignancies associated therewith, can be found in Table 1.

TABLE 1

| Tumor-Specific Antigens and Associated Malignancies | |
| --- | --- |
| Target Antigen | Associated Malignancy |
| α-Folate Receptor | Ovarian Cancer |
| CAIX | Renal Cell Carcinoma |
| CD19 | B-cell Malignancies |
| | Chronic lymphocytic leukemia (CLL) |
| | B-cell CLL (B-CLL) |
| | Acute lymphoblastic leukemia (ALL); ALL post Hematopoietic stem cell transplantation (HSCT) |
| | Lymphoma; Refractory Follicular Lymphoma; B-cell non-Hodgkin |

TABLE 1-continued

Tumor-Specific Antigens and Associated Malignancies

| Target Antigen | Associated Malignancy |
|---|---|
| | lymphoma (B-NHL) |
| | Leukemia |
| | B-cell Malignancies post-HSCT |
| | B-lineage Lymphoid Malignancies post umbilical cord blood transplantation (UCBT) |
| CD19/CD20 | Lymphoblastic Leukemia |
| CD20 | Lymphomas |
| | B-Cell Malignancies |
| | B-cell Lymphomas |
| | Mantle Cell Lymphoma |
| | Indolent B-NHL |
| | Leukemia |
| CD22 | B-cell Malignancies |
| CD30 | Lymphomas; Hodgkin Lymphoma |
| CD33 | AML |
| CD44v7/8 | Cervical Carcinoma |
| CD138 | Multiple Myeloma |
| CD244 | Neuroblastoma |
| CEA | Breast Cancer |
| | Colorectal Cancer |
| CS1 | Multiple Myeloma |
| EBNA3C | EBV Positive T-cells |
| EGP-2 | Multiple Malignancies |
| EGP-40 | Colorectal Cancer |
| EpCAM | Breast Carcinoma |
| Erb-B2 | Colorectal Cancer |
| | Breast Cancer and Others |
| | Prostate Cancer |
| Erb-B 2, 3, 4 | Breast Cancer and Others |
| FBP | Ovarian Cancer |
| Fetal Acetylcholine Receptor | Rhabdomyosarcoma |
| GD2 | Neuroblastoma |
| GD3 | Melanoma |
| GPA7 | Melanoma |
| Her2 | Breast Carcinoma |
| | Ovarian Cancer |
| | Tumors of Epithelial Origin |
| Her2/new | Medulloblastoma |
| | Lung Malignancy |
| | Advanced Osteosarcoma |
| | Glioblastoma |
| IL-13R-a2 | Glioma |
| | Glioblastoma |
| | Medulloblastoma |
| KDR | Tumor Neovasculature |
| k-light chain | B-cell Malignancies |
| | B-NHL, CLL |
| LeY | Carcinomas |
| | Epithelial Derived Tumors |
| L1 Cell Adhesion Molecule | Neuroblastoma |
| MAGE-A1 | Melanoma |
| Mesothelin | Various Tumors |
| MUC1 | Breast Cancer; Ovarian Cancer |
| NKG2D Ligands | Various Tumors |
| Oncofetal Antigen (h5T4) | Various Tumors |
| PSCA | Prostate Carcinoma |
| PSMA | Prostate/Tumor Vasculature |
| TAA Targeted by mAb IgE | Various Tumors |
| TAG-72 | Adenocarcinomas |
| VEGF-R2 | Tumor Neovasculature |

In some embodiments, the CAR targets CD19, CD33 or CSPG-4.

In examples, variant polypeptides are made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

Optionally, the CAR targets an antigen associated with a specific cancer type. Optionally, the cancer is selected from the group consisting of leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

In some embodiments, a polynucleotide encoding a CAR is mutated to alter the amino acid sequence encoding for CAR without altering the function of the CAR. For example, polynucleotide substitutions leading to amino acid substitutions at "non-essential" amino acid residues can be made in the CARs disclosed above. CARs can be engineered as described, for example, in Patent Publication Nos. WO 2014039523; US 20140242701; US 20140274909; US 20130280285; and WO 2014099671, each of which is incorporated herein by reference in its entirety. Optionally, the CAR is a CD19 CAR, a CD33 CAR or CSPG-4 CAR.

Additional Modifications—Cytokines

In some embodiments, CAR-expressing CIK NKT cells are further modified to express at least one cytokine. In specific embodiments, the at least one cytokine is IL-2, IL-12, IL-15, IL-18, IL-21 or a variant thereof. In preferred embodiments, the cytokine is IL-12. A representative polypeptide of IL-12 comprises or consists of an amino acid sequence set forth in Accession No. IF45_A (https://www.ncbi.nlm.nih.gov/protein/1F45_A) and an amino acid sequence set forth in Accession No. IF45_B (https://www.ncbi.nlm.nih.gov/protein/1F45_B).

Therapeutic Applications

This disclosure also provides a method to treat any type of cancer in a subject at any stage of the disease. Non-limiting examples of the suitable cancers include carcinoma, melanoma, or sarcoma. In some embodiments, the invention is used to treat cancer of hemopoietic origin such as leukemia or lymphoma. In some embodiments, the cancer is a solid tumor.

In some embodiments, the method to treat any type of cancer in a subject comprises administering to the patient a therapeutically effective amount of CIK NKT cells, wherein the thereby treating cancer. The CIK NKT cells are from a population of CIK NKT cells, wherein greater than 90% of the cells in the population express CD 56 and CD3 and less than 10% of the cells in the population express Vα24.

The disclosure also provides a method to treat any type of viral infection, the method comprising administering to the patient a therapeutically effective amount of CIK NKT cells, wherein the thereby treating cancer. The CIK NKT cells are from a population of CIK NKT cells, wherein greater than 90% of the cells in the population express CD 56 and CD3 and less than 10% of the cells in the population express Vα24.

Also provided are methods of treating a subject in need thereof with CIK NKT cells as described herein. In some embodiments, the subject or patient is suffering from cancer or an infectious disease, such as a viral infection.

The CIK NKT cells can be administered to an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) CIK NKT cells per injection, or any ranges between any two of the numbers, end points inclusive. Therefore, this disclosure also provides a composition comprising a plurality of CIK NKT cells, wherein the number of cells are $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth).

In other embodiments, said individual can be administered from about 1000 cells/injection/m$^2$ to up to about 10 billion cells/injection/m$^2$, such as at about, at least about, or at most about, $1\times10^8$/m$^2$, $1\times10^7$/m$^2$, $5\times10^7$/m$^2$, $1\times10^6$/m$^2$, $5\times10^6$/m$^2$, $1\times10^5$/m$^2$, $5\times10^5$/m$^2$, $1\times10^4$/m$^2$, $5\times10^4$/m$^2$, $1\times10^3$/m$^2$, $5\times10^3$/m$^2$ (and so forth) CIK NKT cells per injection, or any ranges between any two of the numbers, end points inclusive.

In other embodiments, CIK NKT cells can be administered to such individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth) CIK NKT cells per kilogram of the individual, or any ranges between any two of the numbers, end points inclusive.

In other embodiments, the total dose may be calculated by m$^2$ of body surface area, including about $1\times10^{11}$, $1\times10^{10}$, $1\times10^9$, $1\times10^8$, $1\times10^7$, per m$^2$, or any ranges between any two of the numbers, end points inclusive. The average person is about 1.6 to about 1.8 m$^2$. In a preferred embodiment, between about 1 billion and about 3 billion CIK NKT cells are administered to a patient. In other embodiments, the amount of CIK NKT cells injected per dose may calculated by m$^2$ of body surface area, including $1\times10^{11}$, $1\times10^{10}$, $1\times10^9$, $1\times10^8$, $1\times10^7$, per m$^2$. The average body surface area for a person is 1.6-1.8 m$^2$.

In other embodiments, CIK NKT cells can be administered to such individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, or $5\times10^3$ (and so forth) CIK NKT cells per kilogram of the individual, or any ranges between any two of the numbers, end points inclusive.

CIK NKT cells can be administered once to a patient with cancer or they can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In some embodiments, CIK NKT cells are administered in a composition comprising the CIK NKT cells and a medium, such as human serum or an equivalent thereof. In some embodiments, the medium comprises human serum albumin. In some embodiments, the medium comprises human plasma. In some embodiments, the medium comprises about 1% to about 15% human serum or human serum equivalent. In some embodiments, the medium comprises about 1% to about 10% human serum or human serum equivalent. In some embodiments, the medium comprises about 1% to about 5% human serum or human serum equivalent. In a preferred embodiment, the medium comprises about 2.5% human serum or human serum equivalent. In some embodiments, the serum is human AB serum. In some embodiments, a serum substitute that is acceptable for use in human therapeutics is used instead of human serum. Such serum substitutes may be known in the art, or developed in the future. Although concentrations of human serum over 15% can be used, it is contemplated that concentrations greater than about 5% will be cost-prohibitive. In some embodiments, CIK NKT cells are administered in a composition comprising CIK NKT cells and an isotonic liquid solution that supports cell viability. In some embodiments, CIK NKT cells are administered in a composition that has been reconstituted from a cryopreserved sample.

Pharmaceutically acceptable compositions comprising the CIK NKT cells can include a variety of carriers and excipients. A variety of aqueous carriers can be used, e.g., buffered saline and the like. These solutions are sterile and generally free of undesirable matter. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable is used synonymously with physiologically acceptable and pharmacologically acceptable. A pharmaceutical composition will generally comprise agents for buffering and preservation in storage and can include buffers and carriers for appropriate delivery, depending on the route of administration.

These compositions for use in in vivo or in vitro may be sterilized by sterilization techniques employed for cells. The compositions may contain acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cells in these formulations and/or other agents can vary and will be selected primarily based on fluid volumes, viscosities, body weight and the like in accordance with the particular mode of administration selected and the subject's needs.

In one embodiment, CIK NKT cells are administered to the patient in conjunction with one or more other treatments or agent for the cancer being treated. In some embodiments, the one or more other treatments for the cancer being treated include, for example, an antibody, radiation, chemotherapeutic, stem cell transplantation, or hormone therapy.

In some embodiments, CIK NKT cells and the other cancer agent/treatment are administered simultaneously or approximately simultaneously (e.g., within about 1, 5, 10, 15, 20, or 30 minutes of each other). In some embodiments, the CIK NKT cells and the other cancer agent/treatment are administered sequentially. In some embodiments, the other cancer treatment/agent is administered one, two, or three days after the administration of the CIK NKT cells.

In one embodiment, the other cancer agent is an antibody. In one embodiment, CIK NKT cells are administered in conjunction with an antibody targeting the diseased cells. In one embodiment, CIK NKT cells and an antibody are administered to the patient together, e.g., in the same formulation; separately, e.g., in separate formulations, concurrently; or can be administered separately, e.g., on different dosing schedules or at different times of the day. When administered separately, the antibody can be administered via any suitable route, such as intravenous or intra-tumoral injection.

In some embodiments, CIK NKT cells of the present disclosure are used in combination with therapeutic antibodies and/or other anti-cancer agents. Therapeutic antibodies may be used to target cells that express cancer-associated or tumor-associated markers. Examples of cancer therapeutic monoclonal antibodies are shown in Table 2.

TABLE 2

Illustrative therapeutic monoclonal antibodies
Examples of FDA-approved therapeutic monoclonal antibodies

| Antibody | Brand name | Company | Target | Indication (Targeted disease) |
|---|---|---|---|---|
| Alemtuzumab | Campath ® | Genzyme | CD52 | Chronic lymphocytic leukemia |
| Brentuximab vedotin | Adcetris ® | | CD30 | Anaplastic large cell lymphoma (ALCL) and Hodgkin lymphoma |
| Cetuximab | Erbitux ® | Bristol-Myers Squibb/Eli Lilly/Merck KGaA | epidermal growth factor receptor | Colorectal cancer, Head and neck cancer |
| Gemtuzumab | Mylotarg ® | Wyeth | CD33 | Acute myelogenous leukemia (with calicheamicin) |
| Ibritumomab tiuxetan | Zevalin ® | Spectrum Pharmaceuticals, Inc. | CD20 | Non-Hodgkin lymphoma (with yttrium-90 or indium-111) |
| Ipilimumab (MDX-101) | Yervoy ® | | blocks CTLA-4 | Melanoma |
| Ofatumumab | Arzerra ® | | CD20 | Chronic lymphocytic leukemia |
| Palivizumab | Synagis ® | MedImmune | an epitope of the RSV F protein | Respiratory Syncytial Virus |
| Panitumumab | Vectibix ® | Amgen | epidermal growth factor receptor | Colorectal cancer |
| Rituximab | Rituxan ®, Mabthera ® | Biogen Idec/Genentech | CD20 | Non-Hodgkin lymphoma |
| Tositumomab | Bexxar ® | GlaxoSmithKline | CD20 | Non-Hodgkin lymphoma |
| Trastuzumab | Herceptin ® | Genentech | ErbB2 | Breast cancer |
| Blinatunomab | | | bispecific CD19-directed CD3 T-cell engager | Philadelphia chromosome-negative relapsed or refractory B cell precursor acute lymphoblastic leukemia (ALL) |
| Avelumamab | | | anti-PD-L1 | Non-small cell lung cancer, metastatic Merkel cell carcinoma; gastric cancer, breast cancer, ovarian cancer, bladder cancer, melanoma, meothelioma, including metastatic or locally advanced solid tumors |
| Daratumumab | | | CD38 | Multiple myeloma |
| Elotuzumab | | | a SLAMF7-directed (also known as CD 319) immunostimulatory antibody | Multiple myeloma |

Administration of such CIK NKT cells may be carried out simultaneously with the administration of the monoclonal antibody, or in a sequential manner. In some embodiments, the CIK NKT cells are administered to the subject after the subject has been treated with the monoclonal antibody. Alternatively, the CIK NKT cells may be administered at the same time, e.g., within 24 hours, of the monoclonal antibody.

In some embodiments, CIK NKT cells are administered intravenously. In some embodiments the CIK NKT cells are infused directly into the bone marrow.

Therefore, this disclosure provides a method of treating cancer or viral infection in a patient in need thereof, the method comprising administering to the patient a therapeutically effective amount of CIK NKT cells from the population of CIK NKT cells using the methods disclosed herein to thereby treating cancer Kits Also disclosed are kits for the treatment of cancer or an infectious disease using compositions comprising an amount of CIK NKT cells as described herein. In some embodiments, the kits of the present disclosure may also include at least one monoclonal antibody.

In certain embodiments, the kit may contain additional compounds such as therapeutically active compounds or drugs that are to be administered before, at the same time or after administration of CIK NKT cells. Examples of such compounds include an antibody, vitamins, minerals, fludrocortisone, ibuprofen, lidocaine, quinidine, chemotherapeutic, etc.

In various embodiments, instructions for use of the kits will include directions to use the kit components in the treatment of a cancer or an infectious disease. The instructions may further contain information regarding how to CIK NKT cells (e.g., thawing and/or culturing). The instructions may further include guidance regarding the dosage and frequency of administration.

In certain embodiments, the kit further comprises one or more containers filled with one or more compositions described herein, e.g., a composition comprising CIK NKT cells as described herein. Optionally associated with such containers can be a label indicating the kit is for treating a cancer, such as those described herein. Optionally the label also includes a notice in the form prescribed by a governmental agency regulating the manufacture, use or sale of pharmaceuticals or biological products, which notice reflects approval by the agency of manufacture, use or sale for human administration.

The present disclosure and the working examples exemplifies producing and using CIK NKT cells derived from cord blood samples, one or ordinary skill in the art would appreciate that CIK NKT cells can also be generated from other hematopoietic progenitor cell samples using similar approaches to the ones described herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Examples

This disclosure comprises the following, non-limiting embodiments.

Embodiment 1. A population of CIK NKT cells, wherein greater than 50% of the cells in the population express CD 56 and CD3 and less than 10% of the cells in the population express Va24.

Embodiment 2. The population of CIK NKT cells of embodiment 1, wherein the CIK NKT cells can kill a target cell in the absence of alpha-galactosylceramide (Gal-Cer).

Embodiment 3. The population of CIK NKT cells of embodiment 1, wherein the target cell is a cancer cell.

Embodiment 4. The population of CIK NKT cells of embodiment 1, wherein the cancer cell line is selected from the group consisting of a myelogenous leukemia cell, a medulloblastoma cell, and a monocytic cell.

Embodiment 5. The population of CIK NKT cells of embodiment 3, wherein the cancer cell is selected from the group consisting of a K562 cell, a Daudi cell, a DAOY cell, and a THP-1 cell.

Embodiment 6. The population of CIK NKT cells of embodiments 2-5, wherein the CIK NKT cells kill a plurality of the target cells at an EC50 of between 1.0 and 10.0.

Embodiment 7. The population of CIK NKT cells of embodiments 6, wherein the CIK NKT cells can kill the target cells at a EC50 that is no less than 90% and no greater than 110% of the EC50 at which the CIK NKT cells killing the target cells in the presence of Gal-Cer.

Embodiment 8. A composition comprising a plurality of CIK NKT cells from the population of CIK NKT cells of any of embodiments 1-7, and a physiologically acceptable excipient.

Embodiment 9. A kit for treating cancer comprising a plurality of CIK NKT cells from the population of CIK NKT cells of any of embodiments 1-7, wherein the kit further comprises a container and/or a label indicating the kit is for treating cancer.

Embodiment 10. A method of enriching CIK NKT cells from a cord blood sample, the method comprising: isolating mononuclear cells from the cord blood sample; and contacting the isolated mononuclear cells with one or more agents selected from the group consisting of IL-7, ALT-803 or IL-15, FLT3 ligand, and Gal-Cer, whereby enriching CIK NKT cells.

Embodiment 11. The method of embodiment 10, wherein the IL-7, if present, is in a concentration ranging from 5 to 20 ng/mL.

Embodiment 12. The method of embodiment 10 or 11, wherein the ALT-803, if present, is in a concentration ranging from 100 to 300 ng/mL.

Embodiment 13. The method of any of embodiments 10-12, wherein the FLT3 ligand, if present, is in a concentration ranging from 5 to 20 ng/mL.

Embodiment 14. The method of any of embodiments 10-13, wherein the Gal-Cer is present in a concentration ranging from 2 to 10 µg/mL.

Embodiment 15. The method of embodiment 10, wherein the method further comprises isolating the enriched CIK NKT cells from the rest of the cord blood sample.

Embodiment 16. The method of embodiment 15, wherein the method further comprises contacting the isolated CIK NKT cells with anti-CD3, anti-CD28, and IL2 to expand the CIK NKT cells.

Embodiment 17. The method of embodiment 16, wherein the method further comprises contacting the isolated CIK NKT cells with Gal-Cer.

Embodiment 18. The method of embodiment 17, wherein the Gal-Cer is a present in a form of a Gal-Cer loaded CD1d tetramer.

Embodiment 19. The method of embodiment 16, wherein the anti-CD3 antibody is present in an amount of 5 ng/mL to 60 ng/mL.

Embodiment 20. The method of any of embodiments 16-19, wherein the anti-CD28 antibody is present in an amount of 0.1 μg/mL to 2 μg/mL.

Embodiment 21. The method of any of embodiments 16-20, wherein IL-2 is present in a concentration of 50 ng/mL to 500 ng/mL.

Embodiment 22. The method of any of embodiments 16-21, wherein the production of CIK NKT cells does not include interferon-gamma.

Embodiment 23. A method of treating cancer or viral infection in a patient in need thereof, the method comprising administering to the patient a therapeutically effective amount of CIK NKT cells from the population of CIK NKT cells of any of embodiments 1-7, thereby treating cancer.

Embodiment 24. The method of embodiment 23, wherein about $1\times10^8$ to about $1\times10^{11}$ cells per $m^2$ of body surface area of the patient are administered to the patient.

Embodiment 25. The method of embodiment 23, wherein the cancer is selected from the group consisting of a leukemia, a lymphoma, polycythemia vera, multiple myeloma, Waldenstrom's macroglobulinemia, heavy chain disease, a sarcoma and a carcinoma.

Embodiment 26. The method of embodiment 25, wherein the cells are administered to the patient by a route selected from the group consisting of intravenous, intraperitoneal, and subcutaneous.

Embodiment 27. The method of any of embodiments 23-26, wherein the method further comprises administering an antibody.

Embodiment 28. A population of CIK NKT cells produced by the methods of any of embodiments 10-27.

Embodiment 29. The population of CIK NKT cells of embodiment 1, wherein the CIK NKT cells express a CAR and/or a cytokine.

EXAMPLES

The following examples are for illustrative purposes only and should not be interpreted as limitations. There are a variety of alternative techniques and procedures available to those of skill in the art which would similarly permit one to successfully perform the examples below.

Example 1: Phenotypes of CIK-NKT Cells

Figure 1:
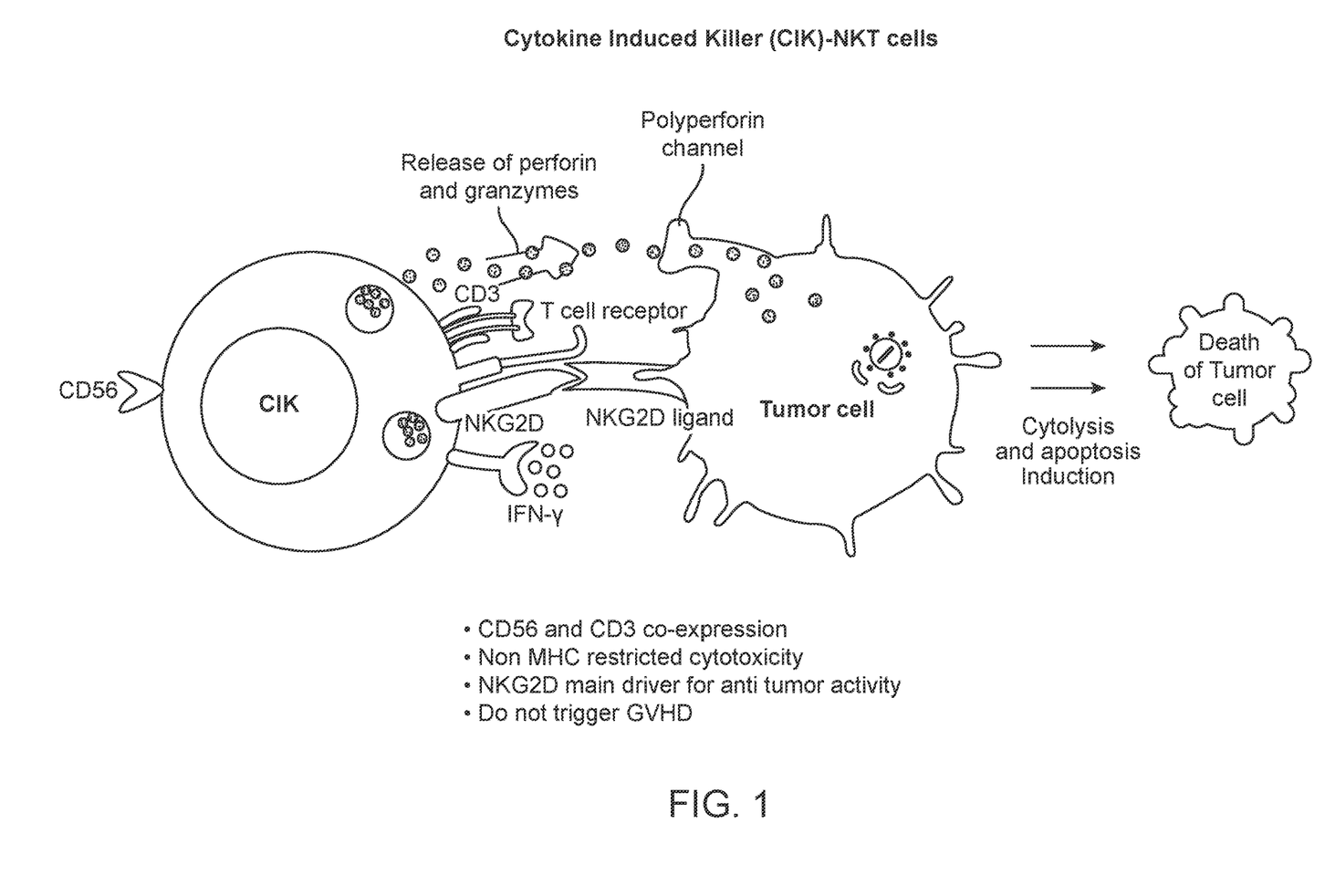
FIG. 1 is a schematic representation of the pathway which CIK NKT cells employ to kill target cells.
Figure 2A:
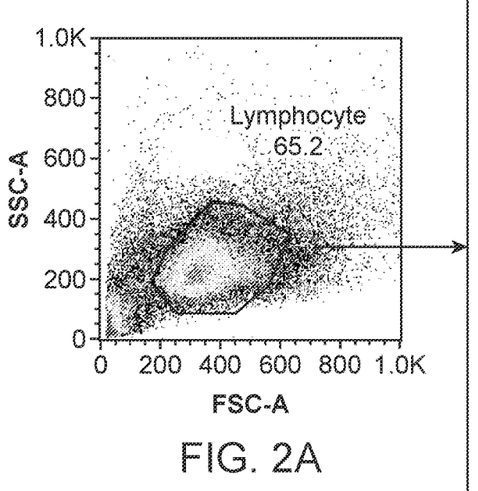
FIG. 2A is the forward scatter and size scatter diagram.
Figure 2B:
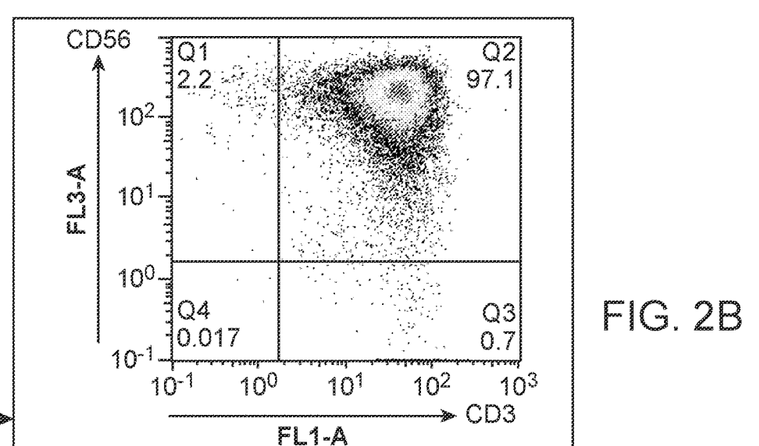
FIG. 2B shows CD3 and CD56 diagrams.
Figure 2C:
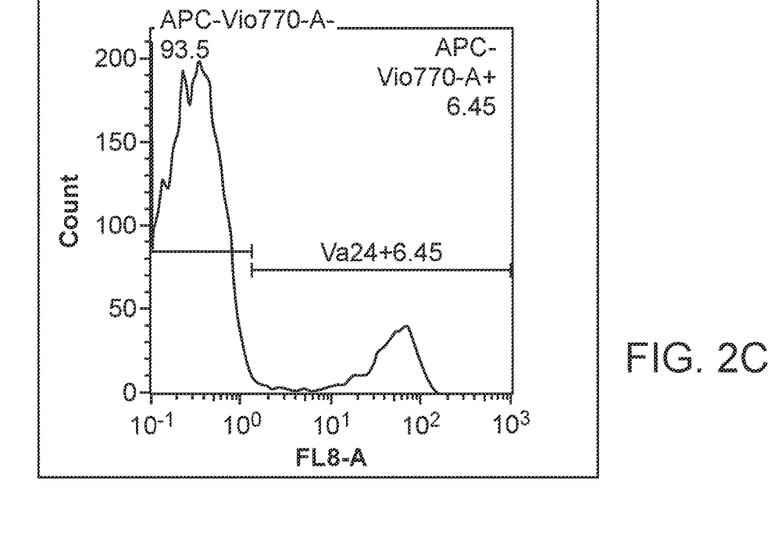
FIG. 2C shows the Va24 diagram.

Cord blood mononuclear cells (Comics) were isolated from cord blood samples by density gradient method using Ficoll-Paque and Sepmate™, from Stem cell Technology Inc. Comics were incubated with Gal-Cer (5 μg/mL), FLT3-L (10 ng/mL), IL-7 (10 ng/mL), and ALT-803 (175 ng/mL) for enrichment of NKT for 2 weeks in RPMI medium with 10% Human AB serum. NKT cells were isolated by affinity chromatography using reagents from Miltenyi Biotec, Germany. Subsequently, isolated cells were expanded in the presence of anti-CD3 antibody (20 ng/mL), anti-CD28 antibody (0.5 μg/mL), and IL2 (200 ng/mL) in the NK Macs medium with 10% Human AB serum for overnight activation with Gal-Cer loaded CD1d tetramer. The Gal-Cer loaded CD1d tetramer was from ProImmune, Oxford, UK and was used in an amount such that the Gal-Cer was present in an amount of 100 ng/mL Upon a week of expansion, these cells were stained with antibodies recognizing CD3, CD56, or Va24. The results show that a majority of the cells (97.1%) were positive for both CD56 and CD3 (FIG. 2B) and a small percentage of cells (6.45%) were positive for Va24 (FIG. 2C). This indicates that cord blood CIK NKT cells have low Va24 expression but the expression of CD3 and CD56 remain intact.

Example 2: Cytotoxicity of CIK NKT Cells is Independent of Gal-Cer

The NKT-CIK cells prepared as described in Example 2 were assessed for cytotoxicity against cancer cell line DAOY. DAOY cells were incubated with Gal-Cer at 1 μg/mL overnight. The Gal-Cer treated DAOY Cells were then incubated with a fluorescent dye, Calcien AM, for 30 min. The cells were washed and then incubated with CB-NKT CIKs, at various effector to target ratios as indicated (the highest ratio was 32:1), for 4 hours. The killing of the DAOY cells was measured by the cell lysis, which is represented by the amount of CalcienAM dye released from cells. FIG. 3A shows the amount of CalcienAM dye released from DAOY cells caused by the CB-NKT CIKs. Data were presented as % lysis of target cells. The results show that there were significant difference in terms of killing between the group in which target cell were loaded with Gal-Cer and the group in which target cells were not loaded with Gal-Cer, indicating that Gal-Cer treatment did not confer killing specificity.

FIG. 3B compares the cytotoxicity of NKT-CIK cells derived from cord blood as described above (CB-CIK NKT cells) versus PBiNKT cells (iNKT cells isolated from peripheral blood) on a luciferase-expressing THP1 cells. PBiNKT cells were isolated in the same manner as the CB-CIK NKT cells (see Example 1) except that the source is peripheral blood instead of cord blood. The THP1 cells were co-cultured with CB-CIK NKT cells or PBiNKT cells at various effector to target ratios as indicated, the highest ratio being 32:1. No Gal-Cer was used in this experiment. The results show that CB-CIK NKT cells are more potent in killing THP-1 than do PBiNKT cells.

Example 3: Cytotoxicity of CIK NKT Cells on K562 and Daudi Cells

Figure 4:
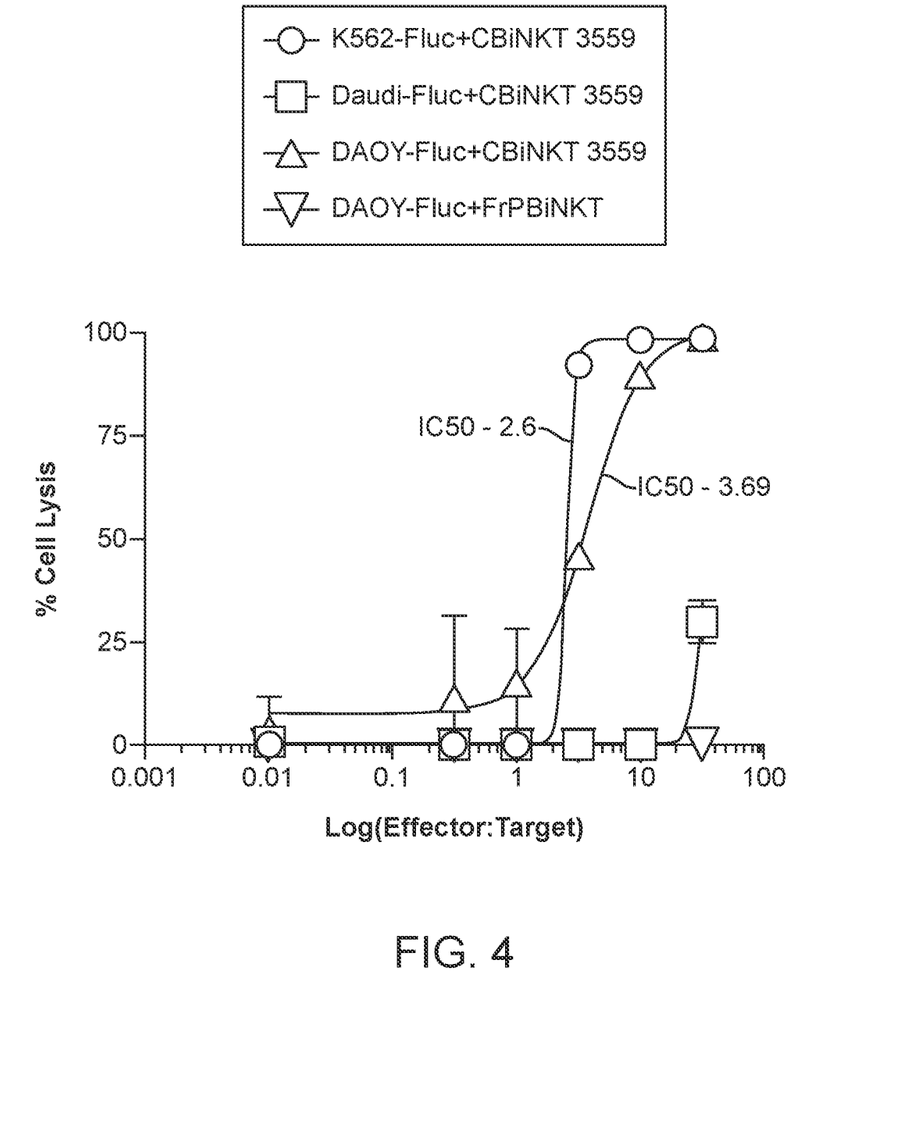
FIG. 4 shows the killing of K562 cells, DAOY cells, and Daudi cells by cord blood CIK NKT cells.

CB-NKT CIK cells obtained as above were assayed for their ability to kill luciferase-expressing cancer cell lines, DAOY, Daudi, and K562 (represented by triangles, squares, and circles, respectively, in FIG. 4). Peripheral blood isolated iNKTs were used as control (inverted triangles in FIG. 4). Cell killing assays were performed after 4-hour of co-culturing of the cancer cells and effector cells (CB CIK NKTs or PBiNKTs). The killing of the cancer cells was measured by % of cell lysis, which was represented by the loss of luciferase in these cancer cell lines. Various effector to target ratios were used as indicated, the highest being 32:1. The results indicate that CB-CIK NKT cells kill target cells in a non CD1d/MHC restricted manner.

What is claimed is:
1. A method of obtaining a population of CIK NKT cells, in which greater than 90% of the CIK NKT cells express CD56 and CD3 and less than 10% of the CIK NKT cells express Va24 from a blood sample, the method comprising: isolating mononuclear cells from the blood sample; and contacting the isolated mononuclear cells with i) IL-7, ii) ALT-803 or IL-15, iii) FLT3 ligand, and iv) Gal-Cer.

2. The method of claim 1, wherein the IL-7 is present in a concentration ranging from 5 to 20 ng/mL.

3. The method of claim 1, wherein the ALT-803, if present, is in a concentration ranging from 100 to 300 ng/mL.

4. The method of claim 1, wherein the FLT3 ligand is present in a concentration ranging from 5 to 20 ng/mL.

5. The method of claim 1, wherein the Gal-Cer is present in a concentration ranging from 2 to 10 µg/mL.

6. The method of claim 1, wherein the method further comprises isolating the enriched CIK NKT cells from the rest of the blood sample.

7. The method of claim 6, wherein the method further comprises expanding the isolated CIK NKT cells with an anti-CD3 antibody, anti-CD28 antibody, and IL2.

8. The method of claim 7, wherein the Gal-Cer is present in a form of a Gal-Cer loaded CD1d tetramer.

9. The method of claim 7, wherein the anti-CD3 antibody is present in an amount of 5 ng/mL to 60 ng/mL.

10. The method of claim 7, wherein the anti-CD28 antibody is present in an amount of 0.111 g/mL to 2 µg/mL.

11. The method of claim 7, wherein IL-2 is present in a concentration of 50 ng/mL to 500 ng/mL.

12. The method of claim 7, wherein the obtaining of CIK NKT cells does not include interferon-gamma.

13. The method of claim 7, wherein the population of expanded CIK NKT cells comprise cytotoxic effector cells that are cytotoxic in the absence of Gal-Cer.

14. The method of claim 7, wherein greater than 90% of the population of expanded CIK NKT cells express CD56 and CD3, and less than 10% of the population express Va24.

15. A method of producing a population of CIK NKT cells from a blood sample, in which greater than 90% of the CIK NKT cells express CD56 and CD3 and less than 10% of the CIK NKT cells express Va24, the method comprising: 1) isolating mononuclear cells from the blood sample; and contacting the isolated mononuclear cells with IL-7, ALT-803 or IL-15, or FLT3 ligand, and Gal-Cer, thereby enriching the CIK NKT cells; 2) isolating the enriched CIK NKT cells from the rest of the blood sample; and 3) expanding the isolated CIK NKT cells with anti-CD3, anti-CD28, IL2, and Gal-Cer.

* * * * *